(12) United States Patent
Swift et al.

(10) Patent No.: US 8,207,446 B2
(45) Date of Patent: Jun. 26, 2012

(54) NON-METALLIC, INTEGRATED SENSOR-INTERCONNECT DEVICE, MANUFACTURING PROCESS, AND RELATED APPLICATIONS

(75) Inventors: Joseph A. Swift, Ontario, NY (US); Stanley J. Wallace, Victor, NY (US); Roger Lee Bullock, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 549 days.

(21) Appl. No.: 12/402,717

(22) Filed: Mar. 12, 2009

(65) Prior Publication Data

US 2010/0230132 A1 Sep. 16, 2010

(51) Int. Cl.
 *H01B 3/00* (2006.01)
(52) U.S. Cl. ................................................ 174/110 R
(58) Field of Classification Search .............. 174/110 R, 174/119 R
 See application file for complete search history.

(56) References Cited

U.S. PATENT DOCUMENTS

| | | | |
|---|---|---|---|
| 4,972,046 A * | 11/1990 | van der Heide | 174/126.1 |
| 5,281,771 A * | 1/1994 | Swift et al. | 174/262 |
| 5,291,888 A | 3/1994 | Tucker et al. | |
| 5,348,006 A | 9/1994 | Tucker | |
| 5,348,397 A * | 9/1994 | Ferrari | 374/185 |
| 5,414,216 A * | 5/1995 | Swift et al. | 174/124 R |
| 6,444,102 B1 * | 9/2002 | Tucci et al. | 204/279 |
| 7,052,763 B2 * | 5/2006 | Swift et al. | 428/300.4 |
| 7,220,131 B1 | 5/2007 | Pecht et al. | |
| 7,612,665 B2 * | 11/2009 | Okada et al. | 340/540 |
| 2003/0110860 A1 * | 6/2003 | Okada | 73/593 |
| 2008/0221456 A1 * | 9/2008 | Babchenko | 600/476 |

\* cited by examiner

*Primary Examiner* — Chau Nguyen
(74) *Attorney, Agent, or Firm* — MH2 Technology Law Group LLP (57) ABSTRACT

Exemplary embodiments provide materials, devices and arrays of integrated sensor assembly, as well as methods for forming and using such devices and arrays in sensing systems. In one embodiment, the integrated sensor assembly can include an interconnecting member and at least one sensor member connected with the interconnecting member at any location thereof. Each of the sensor member and the interconnecting member can include a core element and a polymer. The core element for the sensor member and the core element for the interconnecting member can be electrically interconnected. Various embodiments can also include a connector member connected to the interconnecting member for transmitting sensing signals from or to the sensor member.

10 Claims, 4 Drawing Sheets

NON-METALLIC, INTEGRATED SENSOR-INTERCONNECT DEVICE, MANUFACTURING PROCESS, AND RELATED APPLICATIONS

DESCRIPTION OF THE INVENTION

1. Field of the Invention

This invention relates generally to sensing materials, devices and systems and, more particularly, to non-metallic integrated sensor-interconnect materials, devices, and arrays, as well as methods for their manufacturing and their applications.

2. Background of the Invention

There has been considerable interest in using high value contacts, interconnects, sensors, probes, and the like for use in a wide spectrum of electric test, measure, and control applications in the medical, entertainment, electronics, and other related industries.

For example, a decade ago, fine diameter wire-like microprobes or microelectrodes made from pure carbon fibers were inserted into the stomachs of canine subjects to study the electrochemical characteristics of digestive processes of interest to researchers. More recently, microelectrodes including carbon fiber arrays have been used to probe into optically stimulated electric activity in rabbit retina.

U.S. Pat. Nos. 5,291,888 and 5,348,006 disclose arrays of non-magnetic contact sensors that are held and positioned against the human head by a positioning element such as an elastic cap. The sensors are used for measuring brain anatomy or function. U.S. Pat. No. 7,220,131 discloses electrical interconnect devices including metal overcoated carbon fibers suitable for use in arrays of probes to measure electric signals to and from electronic components, such as semiconductor chips and related packaged assemblies.

Conventional carbon fiber-related sensor devices include a contact sensor at one end of a small diameter insulated conductive wire, which may include a multifilament carbon fiber core element. The connecting wire is configured with a metal pin connector at the other terminal end. The contact sensor is positioned and mounted within a relatively large diameter of a flexible rubber pod, which helps provide a contact loading force between the sensor contact tip and test subject. Ultrasonic and thermal welding is used to join the contact sensor to the free end of the wire's core conductor.

Problems arise, however, due to the following reasons. First, the sonic or thermal welding used to join the wire's core and the contact sensor, and probably to join the contact sensor and the rubber pod, is not robust, because the joints are relatively weak and subject to damage. Numerous electrical and mechanical failures may then occur and cause a short lifetime of the assemblies and require a large number of costly replacement parts. For example, some sensor assemblies fail initially when configured into the desired arrays, while others fail prematurely due to the rigors of normal handling, cleaning, and use. Second, the welding processes are proven to be suitable for low volume laboratory scale fabrication, but there are challenges for providing large-scaled production volumes.

Thus, there is a need to provide a non-metallic integrated sensor-interconnect assembly and related arrays, as well as methods for their manufacturing and applications for sensing systems.

SUMMARY OF THE INVENTION

According to various embodiments, the present teachings include an integrated sensor assembly that includes an interconnecting member and at least one sensor member that is extended from and electrically interconnected with the interconnecting member at any location along the interconnecting member. Each of the at least one sensor member and the interconnecting member can include a polymer and a core element that is substantially non-metallic.

According to various embodiments, the present teachings also include a method for forming an integrated sensor assembly. In the method, a core element can first be provided having a first section and a second section. The core element can also include one or more filaments that are substantially non-metallic and can have a resistivity, for example, ranging from about $1 \times 10 \exp(-4)$ to about $1 \times 10 \exp(10)$ ohm-cm. The first section of the core element can then be composited with a polymer; while at least one jacket band can be formed surrounding the second section of the core element.

According to various embodiments, the present teachings also include a method for forming an integrated sensor assembly. In this method, a composite element can be formed including a core element and one or more binder polymers, wherein the core element can include one or more non-metallic fiber tows. A section of the composite element can then be shaped by reducing one or more dimensions thereof; and one or more jacket bands can be overcoated on the shaped section of the composite element to form a sensor member.

According to various embodiments, the present teachings further include a method for forming an integrated sensor assembly. This method can include a polymer encased member formed to include a polymer overcoat upon a core element, wherein the core element can include one or more filaments with each filament made from at least one non-metallic nanostructure. A portion of the polymer overcoat can be removed from at least one end of the polymer encased member and thereby exposing a corresponding end portion of the core element. A tip region can be formed from the exposed end portion of the core element, the tip region being used as a contact or a probe.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to the present embodiments (exemplary embodiments) of the invention, examples of which are illustrated in the accompanying drawings. Wherever possible, the same reference numbers will be used throughout the drawings to refer to the same or like parts. In the following description, reference is made to the accompanying drawings that form a part thereof and in which is shown by way of illustration specific exemplary embodiments in which the invention may be practiced. These embodiments are described in sufficient detail to enable those skilled in the art to practice the invention and it is to be understood that other embodiments may be utilized and that changes may be made without departing from the scope of the invention. The following description is, therefore, merely exemplary.

While the invention has been illustrated with respect to one or more implementations, alterations and/or modifications can be made to the illustrated examples without departing from the spirit and scope of the appended claims. In addition, while a particular feature of the invention may have been disclosed with respect to only one of several implementations, such feature may be combined with one or more other features of the other implementations as may be desired and advantageous for any given or particular function. Furthermore, to the extent that the terms "including", "includes", "having", "has", "with", or variants thereof are used in either the detailed description and the claims, such terms are intended to be inclusive in a manner similar to the term "comprising." As used herein, the term "one or more of" with respect to a listing of items such as, for example, A and B, means A alone, B alone, or A and B. The term "at least one of" is used to mean one or more of the listed items can be selected.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less that 10" can assume values as defined earlier plus negative values, e.g. −1, −1.2, −1.89, −2, −2.5, −3, −10, −20, −30, etc.

Exemplary embodiments provide materials, devices and arrays of an integrated sensor assembly, as well as methods for forming and using such devices/arrays in sensing systems. In one embodiment, the integrated sensor assembly can include an interconnecting member and at least one sensor member connected with the interconnecting member at any location thereof. Each of the sensor member and the interconnecting member can include a polymer and a core element that is substantially non-metallic. The core element for the sensor member and the core element for the interconnecting member can be the same or different and can be electrically interconnected. The polymer used for the sensor member and for the interconnecting member can be the same or different. Various embodiments can also include a connector member connected to the interconnecting member for transmitting sensing, stimulation, and/or actuation signals from or to the sensor member.

The disclosed integrated sensor assembly can be used in any sensing systems. The sensing systems can be useful, for example, for detecting and recording cell or tissue level signals including recording of relatively large numbers of simultaneous signals from single or small groupings of cells or tissue. The sensing system can also be useful, when combined with suitable tip overcoatings to render them responsive to pH or certain chemicals including inorganic and organic chemicals, or other conditions of interest, such as the presence, absence, or level of x-ray or other radiation. Similarly, in various embodiments, the disclosed sensing system can be useful in, e.g., homeland security applications where there is a need to sense without signal interference for simultaneous x-ray, magnet or electromagnetic energy within the test environment.

In one embodiment, the sensor member can be a non-metallic, non-interactive, and non-invasive sensor member that is fully integrated with a suitably flexible, non-metallic, carbon fiber based, wire-like interconnecting member.

Figure 1:
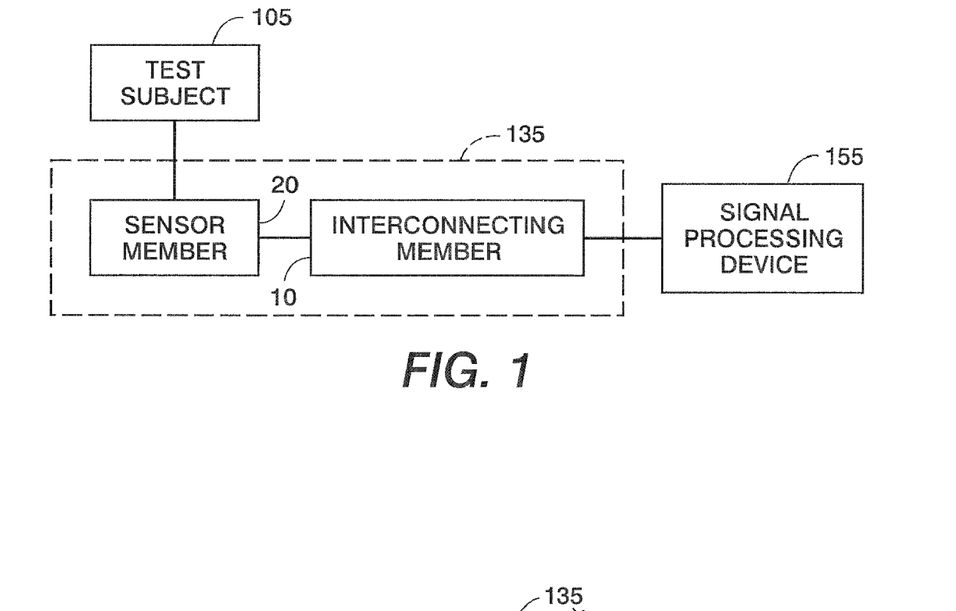
FIG. 1 depicts an exemplary sensing system including an integrated sensor assembly in accordance with the present teachings.

FIG. 1 depicts an exemplary sensing system 100 in accordance with the present teachings. It should be readily apparent to one of ordinary skill in the art that the system 100 depicted in FIG. 1 represents a generalized schematic illustration and that other components/devices can be added or existing components/devices can be removed or modified.

As shown in FIG. 1, the sensing system 100 can include, for example, an integrated sensor assembly 135, and a signal processing device 155. Also shown is a test subject 105

The test subject 105 can include, e.g., any subjects of interest that need to be detected or sensed. In various embodiments, the test subject 105 can include animate or inanimate subjects, that include human, plant, or animal subjects, for example, ocular cellular test subjects, or any bio-species for diagnostic detection and/or drug delivery measured in a cell level or tissue level. Alternately, the test subject 105 can be a synthetic subject, for example, artificial muscle and/or chemical compositions such as electroactive polymers.

The integrated sensor assembly 135 can be operationally placed in contact with the test subject 105, and can further include an interconnecting member 10 connecting with a sensor member 20 at one end of the interconnecting member 10. Specifically, the sensor member 20 of the integrated sensor assembly 135 can be operationally connected with the test subject 105. In one embodiment, the sensor member 20 can provide self-loading and spring-like characteristics, which can provide a reliable contact loading force between at least one contact faces of the sensor member 20 and test subject 105.

The signal processing device 155 can include various electrical devices, such as, for example, a measurement instrument, a display device, a transmitting device, and/or a recording apparatus. The signal processing device 155 can thus include, but is not limited to, a resistor, a liquid crystal display (LCD), a multi-chip module, a printed circuit board (PCB), RFID labels, wireless chips, and/or a printed wiring board (PWB).

Sensing signals detected by the sensor element member 20 can be sent to, received from, and/or transmitted via the integrated interconnecting member 10 (e.g., a wire-like member) to suitable signal processing, device 155, which measures, displays, or records the signal.

The sensor member 20 can be connected to and/or extended from the interconnecting member 10. As used herein, the term "sensor" or "sensor member" refers to a device that responds to physical, electrical, or electronic stimulus and transmits a resulting signal or impulse as for measurement, monitor, or control.

The sensor member 20 can be, e.g., relatively small as compared with the interconnecting member 10, and can be positioned at one end of the interconnecting member 10, or alternatively, at any appropriate location along the interconnecting member 10, e.g., along the length of the interconnecting member 10.

The sensor member 20 can be used to sense and detect the test subject 105. The sensor member 20 can be, for example, a contact sensor. In various embodiments, the sensor member 20 can include, for example, a core element, such as a length of conductive fibrous material, and a polymeric material formed upon the core element as a jacket layer (also referred to herein as an overcoat layer, a sheath layer) and/or composited within the core element as a binder material.

As used herein, the term "interconnecting member" refers to a member that is used for connecting electronic devices/components through which an electrical current, potential, thermal, acoustic, optical or other signal can pass. The interconnecting member 10 can include a core element and an insulating material formed upon the core element as a jacket layer 215 (FIG. 2B, an overcoat layer, or a sheath layer) and/or composited within the core member as a binder polymer.

As disclosed herein, a composite element can be formed when the core element is composited with a polymeric material, for example, the binder polymer and the insulating material as disclosed above. For example, the core element, including fibril-shaped and semi-conductive or conductive elements, can be contained in a suitable polymer to form a composite element, which may have resistive characteristics.

In various embodiments, the polymeric materials used for overcoating and/or compositing the core element for each of the sensor element 20 and the interconnecting element 10 can include, but are not limited to, epoxies, acetals, polyesters, ionic rubbers, non-ionic rubbers, ionic polyurethanes, non-ionic polyurethanes, polyether sulfones, polyether ether ketones, polyether imides, polystyrenes, polyethylene terephthalates, polyamides, polyimides, polyvinylchlorides, polyphenylene oxides, polycarbonates, acrylonitrile-butadiene-styrene terpolymers, silicones, fluropolymers, polyolefins, glasses or ceramics. In various embodiments, the polymeric materials used can contain a fiber or filament, such as a textile filament or textile yarn; and can be configured into a cloth-like or paper-like element so as to provide reinforcement, abrasion resistance, or flexibility, for example, to the outer layer. The filament or yarn in this case can be synthetic, such as polyester, fiberglass, or nylon fiber and the like, and can be natural, such as cotton or silk.

Various processes including, for example, melt thermo-forming, melt draw processing, solution coating, solution dip coating, spin coating, electrodepositing, co-extrusion, electrostatic spray coating, and the like, can be used as overcoating and/or compositing polymer materials upon the core element for each of the sensor element 20 and the interconnecting element 10

In an exemplary embodiment, the jacket layer (or overcoat layer) formed surrounding the core element or the composite formed including the core element within a binder polymer or an insulating material can be prepared by applying polymeric materials in a liquid phase to the core element, followed by a solidification process. The solidification processes can include, for example, curing, freezing, solvent evaporation, or combinations thereof, or other appropriate means, to form the disclosed sensor member and/or the interconnecting member. In an exemplary embodiment, a free length of carbon fiber(s) core element can be solidified with a suitable binder resin, such as an epoxy, silicone, polyurethane, fluoropolymer, and the like. In various embodiments, the core element can be shaped as a hollow element, wherein the hollow portion can allow gas or liquid delivery and/or sampling.

In various embodiments, once solidified, the exemplary polymer bound fiber region can be processed by a secondary process including, for example, cutting or trimming, using a mechanical shear, a waterjet cutting, and/or a laser cutting, in order to achieve a desired final configuration, size, and shape. For larger sensor members or interconnecting members, the secondary process can include, for example, ply laminating, adhesive laminating, insert molding, over-molding, and the like.

In various embodiments, the core element for the sensor member 20 (i.e., sensor core element) and the core element for the interconnecting member 10 (i.e., interconnecting core element) can be the same or different. In one embodiment, the sensor core element can be configured to project out from the insulating layer of the interconnecting member 10 at any location along the interconnecting member. In other embodiment, the sensor core element can be an extended portion (e.g., free length) of the core element of the interconnecting member 10. Suitable polymer(s) can then be combined with the sensor core element to form the sensor member 20. In various embodiments, the sensor core element and the interconnecting core element can be electrically interconnected, regardless the configuration of the sensor member 20 and the interconnecting member 10 the integrated sensor assembly 135. For example, the core element for each of the sensor member 20 and the interconnecting member 10 can have an electrical resistivity ranging from about $1\times10\exp(-5)$ to about $10\times10\exp(12)$ ohm-cm. Alternatively, in certain embodiments, the interconnecting member can have an electrical capacitance and/or an electrical impedance. When operationally coupled with the resistive characteristic, the member can serve to tune, buffer, condition, filter, or manage the signal originating at the sensor member 20 and condition the signal such that it is suitable to match or otherwise match the reception requirements of the signal processing device 155.

In various embodiments, the core element for the interconnecting member 10 and/or for the sensor member 20 can be sufficiently flexible, durable, and capable of withstanding autoclave or other disinfectant cleanings along with the manual or automated handling processes related thereto. In various embodiments, the core element for the interconnecting member 10 and/or the sensor member 20 can be transparent, or at least non-interactive to magnetic, radiological, or electromagnetic fields. Furthermore, the interconnecting core element and/or the sensor core element can be sufficiently electro-conductive and can be used in a continuous length.

In various embodiments, the core element for the interconnecting member 10 and/or the sensor member 20 can include, for example, a single solid strand, such as a carbon nanotube (CNT) filament, boron nitride nanotubular filament, doped silicon fibers, and/or a multi-stranded filament such as a fiber bundle or a fiber tow such as a carbon fiber tow. Similar or different fibers or filaments can be used for the multifilament embodiments.

The single or multi-stranded filaments can be substantially non-metallic and can be made from materials, that are conducting, semi-conducting, or semi-resistive, including, but not limited to, carbon, boron nitride, silicon, boron, doped silicon, boron-carbon, boron-nitride, carbonized synthetic fibers, pitch carbon fibers, polyacrylonitrile carbon fibers, graphite, and the like. The single or multi-stranded filaments can be made from materials in various dimensional scales from macroscopic to microscopic or to nanoscopic dimensions.

The filaments can also include, for example, nanotubes, nanowires, nanoshafts, nanopillars, nanorods, nanoscale plates (e.g., nanoscale graphene plates), nanofibers, nanoneedles, nanofibrils, or other nanostructures that have at least one dimension of about 100 nm or less. Nanosize filler particles, such as nanotubular particles of carbon, can be used, for example, to further modify the operational properties including strength, flexibility, chemical resistance, etc. of the sensor or interconnect. For example, the core element for the interconnecting member 10 and/or for the sensor member 20 can include, one or more nano-sized carbon nanotube (CNT) monofilaments, such as those supplied from NanoComp, Corp. (Concord, N.H.). The nano-sized CNT monofilament can provide strong mechanical strength and/or small scale.

Alternatively, the core element for the interconnecting member 10 and/or the sensor member 20 can include carbon fiber tows containing one or more individual carbon filaments (or fibers). For example, carbon fiber tows having about 1,000 individual filaments can be used in accordance with the present teachings. Other embodiments can include, for example, carbon fiber tows having individual filaments of about 500 or less.

In various embodiments, the core element for the interconnecting member 10 and/or for the sensor member 20 can have at least one dimension, for example, of about 500 microns or less. In an additional example, the at least one dimension can include a diameter of about 0.5 microns to about 500 microns. In another example, the at least one dimension can include a diameter of about 500 nanometers or less, for example, ranging from about 1 nanometer to about 500 nanometers.

In various exemplary embodiments, the interconnecting member 10 can be made from, for example, any suitable carbon fiber or carbon fiber tow that is essentially or even partial non-metallic and/or non-magnetic, as described in related U.S. Pat. No. 4,822,950, entitled "Nickel/Carbon Fiber Braided Shield", which is incorporated herein by reference in its entirety. For example, the interconnecting member 10 can therefore include a shielded electrical conductor unit including a composite having an electrically-conductive carbon core and an electrically-insulating elastomeric jacket surrounding and enveloping the carbon core. In an example, there may be a very thin metallic layer, such as nickel, gold, lead, copper, tin, silver, palladium, platinum or mixtures, blends or alloys thereof, which coats at least a part of the outer layer of the core fiber or at least part of the inner layer of the jacket, or both. The thin layer can have thickness in the range of about 0.1 angstrom to about 1 micron. The metal layers that coat the core and sheath can be the same or different as can be required by the specific applications.

Other exemplary interconnecting members can include those described in related U.S. Pat. No. 5,414,216, entitled "Electrostatographic Reproducing Machine Resistive Carbon Fiber Wire", which is incorporated herein by reference in its entirety. For example, the interconnecting member 10 can include a conductive wire having an electrically conductive core using partially carbonized polyacrylonitrile filaments with a resistivity of between about $1\times10\exp(2)$ and about $1\times10\exp(10)$ ohms-cm. The filaments can be surrounded by an electrically insulating jacket layer. Such interconnecting wire can include the core of from about 2,000 to about 50,000 filaments. The jacket layer can include insulating elastomeric materials such as silicone, and/or insulating polymeric material such as polyester or polyvinyl chloride. The electrically conductive filament core can have a diameter from about 5 microns to about 50 microns.

In a further example, the interconnecting member 10 can include, for example, a lead wire, a shunt wire, a fuse wire, or other wire interconnecting member as known to one of ordinary skill in the art.

Referring back to FIG. 1, in various embodiments, the integrated sensor assembly 135 can further include a connector member (not shown) disposed at one end of the interconnecting member 10, for example, at the end that is opposite to the sensor member 20. In various embodiments, the connector member can be any suitable end-termination, such as a connector to enable connection between the sensor member (along with the interconnecting member) and the signal sensing device 155.

Figure 1A:
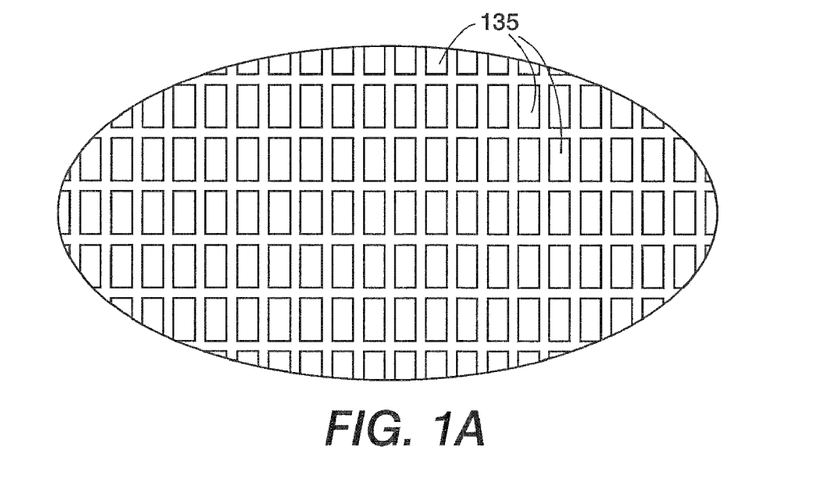
FIG. 1A depicts a portion of an exemplary array of integrated sensor assemblies in accordance with the present teachings.

In various embodiments, the integrated sensor assembly 135 of FIG. 1 can be mass manufactured having arrays of sensor members and/or arrays of integrated sensor assemblies. For example, FIG. 1A shows a portion of an exemplary array of integrated sensor assemblies in accordance with the present teachings. As shown, a plurality of sensor assemblies 135 can be included in the array, which can be used in the disclosed sensing system as shown in FIG. 1 to detect the test subject 105 by the sensor members of the assemblies 135. The sensing signal can then be transmitted by the interconnecting members of the assemblies 135 to the signal processing device 155.

In various embodiments, small dimensions of each member of the exemplary assemblies 135, including the sensor member 20, the interconnecting member 10 and/or the contactor member, can be used, for example, when arrays are used for cell level detection. In various embodiments, the array of integrated sensor assemblies can contain individual sensors or assemblies 135 of, for example, about 2 to about 3000 or more.

Figure 2A:
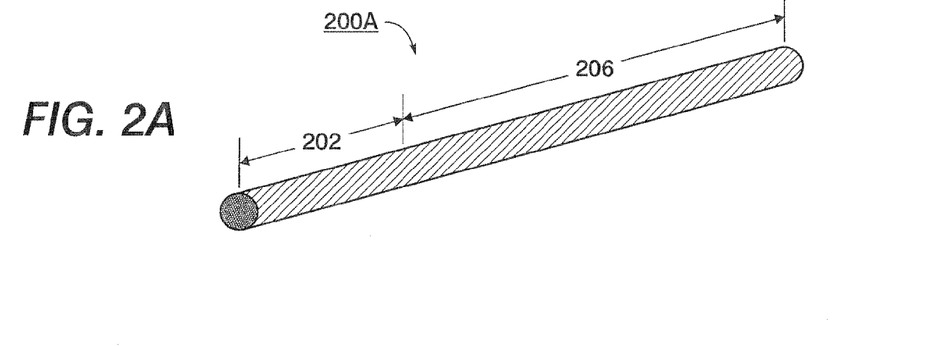
FIGS. 2A-2C depict an exemplary integrated sensor assembly at various stages of formation in accordance with the present teachings.
Figure 2B:
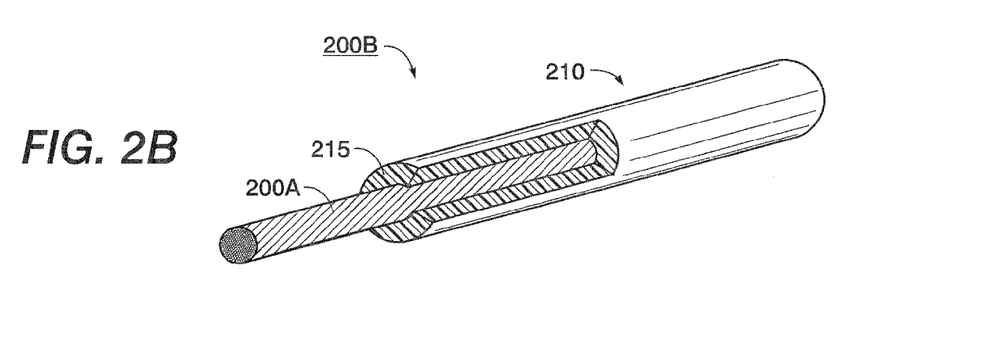
Figure 2C:
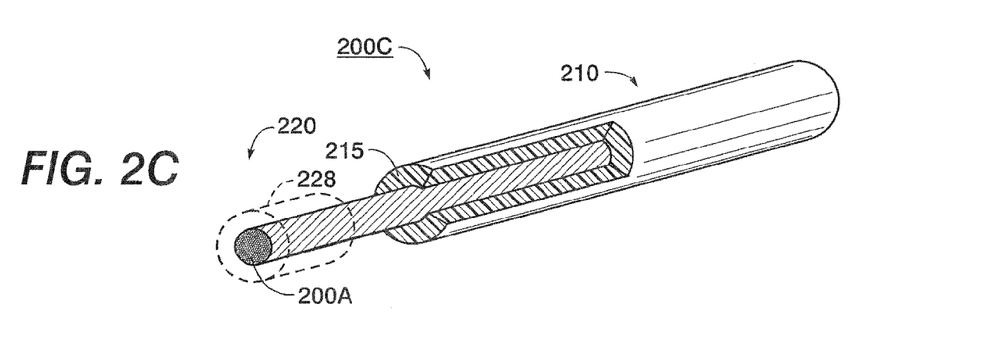

FIGS. 2A-2C depict an exemplary integrated sensor assembly 200A-C at various stages during formation in accordance with the present teachings. It should be readily apparent to one of ordinary skill in the art that the assemblies depicted in FIGS. 2A-2C represent a generalized schematic illustration and that other components/members/devices can be added or existing components/members/devices can be removed or modified.

As shown in FIG. 2A, a core element 200A such as a carbon fiber tow can be provided. The core element can include a resistive carbon fiber tow, for example, having an electrical resistivity ranging from about $1\times10\exp(-4)$ to about $1\times10\exp(10)$ ohm-cm. The carbon fiber tow can have, for example, a circular cross sectional shape, such as an oval or a round shape. In the illustrative example, the carbon fiber tow can be used as a core element for a sensor element and/or for an interconnecting element of the integrated sensor assembly 200. As shown, the core element 200A can be divided into two sections or lengths including a first section 202 (e.g., a short section or length) for a sensor member and a second section 206 (e.g., a long section or length) for the interconnecting member, or vice versa.

In FIG. 2B, a composite section 210 can then be formed including suitable binder polymer(s) or insulating material(s) 215 and the second length 206 (e.g., the long section) of the exemplary carbon fiber tow 200A. In various embodiments, the binder polymer(s) or insulating material(s) 215 can further include a solvent including a volatile solvent to facilitate the compositing process. Various compositing processes known to one of ordinary skill in the art can be used. For example, the composite section 210 can be formed by impregnating a mix of an epoxy binder, e.g., EPON epoxy 862, and a volatile solvent, e.g., toluene, and a suitable crosslinking agent e.g. lindax (Lindau Chemicals) into the exemplary long length 206. The volatile solvent can facilitate the wetting and impregnation processes along with the subsequent evaporation process during the drying and/or curing of the binder polymer impregnated portion of the carbon fiber tows, for example.

Depending on the binder polymer used, the drying or curing process can include, for example, a step-wise process. For example, when epoxy is used, the impregnated portion can first be evaporated at room temperature, and then dried at about 60° C. for one hour, e.g., in a convection oven; the temperature can be increased to about 130° C. and curing can further take place for about one hour. Other curing schedules can be possible depending on the binder polymer and/or solvent used. Curing schedules known to those skilled in the art can be within the scope of embodiments herein.

In various embodiments, the formed composite section 210 can be thin, fiber rich, solid, and mechanically strong. For example, the composite section can have a thickness and/or a width, of about 10 microns to about 1000 mm. Any other thicknesses and/or widths, such as in a nano-scale (e.g., less than 1000) nm or greater than 1000 mm, can also be used for the composite section. In an exemplary embodiment, the composite section can have a rectangular cross section. In other embodiments, the configuration can be circular or round. In other embodiments, the composite section can exhibit, e.g., a spring-like flexible response when compressed along its length-wise axis.

In various embodiments, during the formation of the composite element 210, the remaining length, i.e., the first section 202 (e.g., the short length) of the original core element 200A, e.g., a carbon fiber tow, can remain essentially unchanged during this process.

In FIG. 2C, one or more jacket bands 228 can be formed over the first (e.g., short) section 202 of the exemplary carbon fiber 200A where no composite has been formed. The jacked portion(s) of the first section 202 of the core element 200A can form a sensor member 220 of the integrated sensor assembly 200C.

In various embodiments, prior to the formation of the jacket band(s) 228, the short length 202 of the core element 200A (e.g., the carbon fiber tow), can be processed to have a desired cross-sectional shape and desired dimensions. For example, the first length 202 can be processed by a mechanical compression to change the shape, e.g., from near-oval to a thin, flat and ribbon-like structure. The flat ribbon-like structure can be, e.g., a wide thin layer including a rectangular structure. In various embodiments, the resulting sensor member 220 can have a flat and blunt structure.

The jacket band(s) 228 can then be formed upon the short length 202 of the core element 200A, e.g., the carbon fiber tow, by various coating techniques including, but not limited to, solution coating, dip coating, draw coating, ring coating, and the like. The jacket band(s) 228 can be an insulating jacket layer having a relatively much larger diameter than the core element 200A.

In various embodiments, the exemplary thin rectangular-shaped region, the sensor member 220 having the jacket band(s) 228 formed on the first length 202, can be further size- and shape-modified by one or more secondary processes. The secondary processes can include, for example, cutting or trimming, such as, using a mechanical cutter, mechanical shear, a mechanical shaper, or lathe, a waterjet cutter, and/or a laser cutter, in order to form various desired shapes for specific applications. The final sensor element can become, for example, smaller, containing specific features, or having more flexible elements, after the secondary processes.

In various embodiments, the sensor member 220 can be larger in diameter or in length than the interconnecting member 210 depending on specific applications. For example, the jacket layer 228 can be formed over the long section 206 of the core element 200A to form the sensor member, while the short section 202 of the core element 200A can be composited with binder polymers to form the interconnecting member.

Figure 3A:
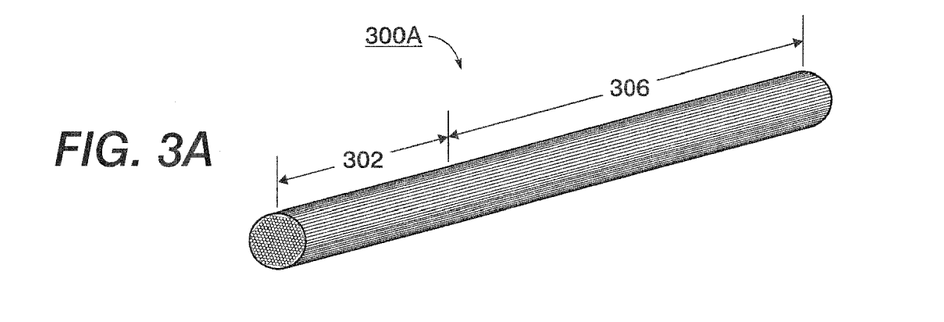
FIGS. 3A-3C depict a second exemplary integrated sensor assembly at various stages of formation in accordance with the present teachings.
Figure 3B:
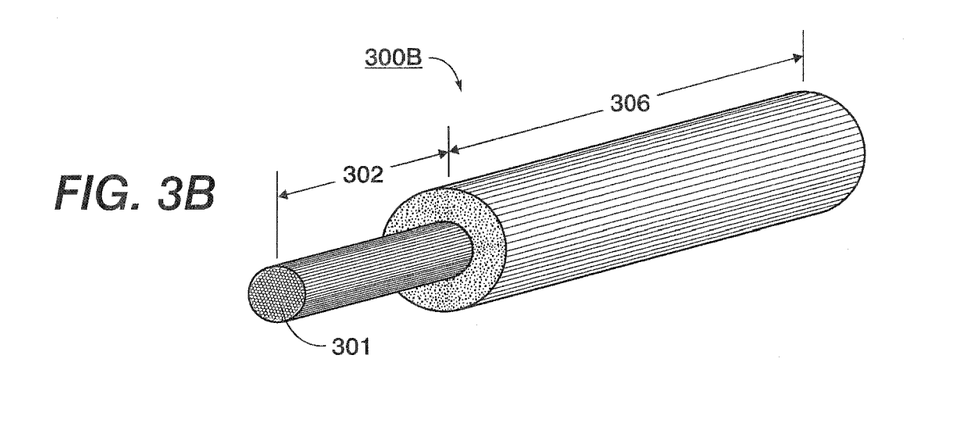
Figure 3C:
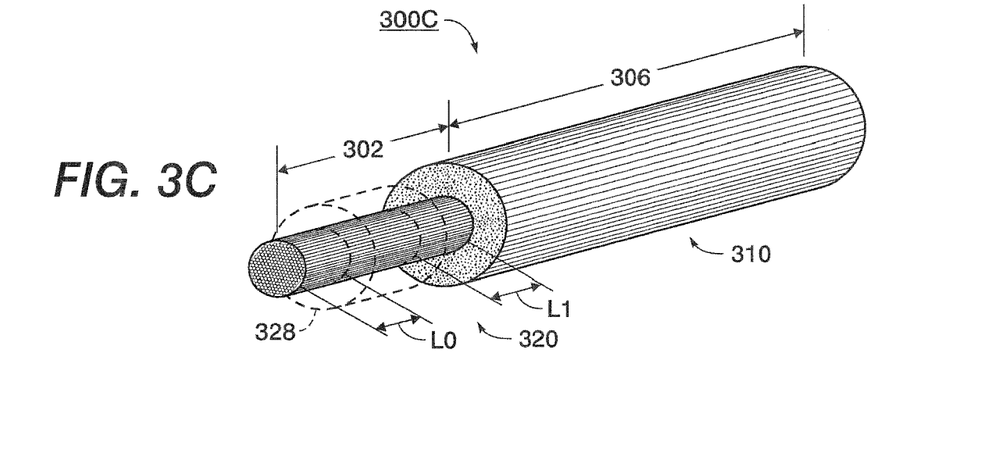

FIGS. 3A-3C depict another exemplary integrated sensor assembly 300 at various stages of formation in accordance with the present teachings. It should be readily apparent to one of ordinary skill in the art that the assemblies depicted in FIGS. 3A-3C represent a generalized schematic illustration and that other components/members/devices can be added or existing components/members/devices can be removed or modified.

In FIG. 3A, a composite element 300A can be formed including a core element, such as one or more carbon fiber tows, secured or composited by binder polymer(s).

The composite element 300A can take a form including, but not limited to, a rod, shaft, sheet, pillar, pipe, tube, hollow body or other semi-finished product or finished product from various composite shaping technologies. In an exemplary embodiment, the composite element 300A can be a composite rod having a diameter of, for example, about 50 microns to about 5 mm.

The composite element 300A can be a composite rod and can have various desired cross section shapes including a circular shape or other shapes. The composite elements and methods for forming the composite elements can include those described in related U.S. patent application Ser. No. 12/055,616, entitled "Composition of Matter for Composite Plastic Contact Elements Featuring Controlled Conduction Pathways, and Related Manufacturing Processes," the disclosure of which is incorporated herein by reference in its entirety. For example, the composite element 300A can be formed by use of a commercial pultrusion process (DFI, Hickory N.C.). In various embodiments, the composite element 300A may not include any volatile solvents, such as the volatile solvent toluene used for the devices and processes in FIGS. 2A-2C.

In various embodiments, the composite element 300A can be mechanically strong and flexible. The composite element 300A can contain carbon fiber tow of about 1% to about 99% by weight of the composite element and contain binder polymers of about 1% to about 99% by weight of the composite element. In an additional example, the composite element 300A can include carbon fiber tow of about 90% to about 98% by weight of the composite element and can include binder polymers of about 2% to about 10% by weight of the composite element.

For preparing the disclosed integrated sensor assembly, the composite element 300A can include a first length 302 for preparing one member of the sensor member and the interconnecting member and a second length 306 for preparing the other member of the sensor member and the interconnecting member.

In FIG. 3B, the first length 302 of the composite element 300A can be processed to provide a desired cross sectional shape and size and flexibility. For example, the first length 302 of the composite element 300A can be milled (e.g., laser milled by Resonetics, Nashua, N.H.) to provide a reduced diameter, which can be used to prepare the sensor member 320 (see FIG. 3C). Optionally, the laser or other suitable waterjet process can be used to remove or eliminate the binder resin form the core fibers thereby increasing the flexibility of the first length 302. The first length 302 of the composite element 300A can have a reduced diameter of about 1% to about 99% of the original diameter. In an exemplary embodiment, a short length can be processed to have a diameter of about 0.012 inches from a composite rod that has an original diameter of about 0.022 inches, in order to form the sensor member.

In FIG. 3C, a sensor member 320 can be formed by overcoating one or more polymer jacket 328 onto the milled first length 302 (e.g., the short section) of the composite element 300A.

The polymeric jacket 328 or overcoat layer can be formed upon the milled first short length 302 by applying a polymeric coating in a liquid form to and then dried upon the first length regions 302. Depending on the polymer used for the over coat, UV light or other radiation can be used to cure the liquid polymer and to solidify the polymer onto the composite element's circumference.

In various embodiments, one or more polymeric overcoat layers 328 can be applied partially or wholly over the first length, which has been processed from the composite element 300A. For example, the polymeric overcoat 328 can be formed as a narrow band located having a length L0 from the fiber-rich tip region 301 and having a length of L1 from the second length 306 of the composite element 300A. In an exemplary embodiment, the polymeric overcoat band can be about 3 mm to about 4 mm (L0) from the processed fiber-rich tip region of the first length and about 5-6 mm (L1) from the second region of the composite rod which is thicker than the milled first region.

In this manner, the region where no overcoat exists can be relatively flexible when compared to the over-coated regions. In various embodiments, the polymeric overcoat layer(s) 328 fabricated upon at least a portion of the periphery of the fiber-rich composite can have any desired pattern(s) and at any location(s) of the first length 302, which provides the feasibility of application. In various further embodiments, the polymer overcoat layer(s) can serve as an interface to facilitate alignment, positioning, and/or attachment of other ancillary devices or features during the fabrication or after the fabrication.

In various embodiments, the tip-most free end 301 projecting out of the polymer encased region can represent a fiber rich member that is suitable for use as contact for the sensor member 320. The contact area of these sensors can be in the range from about 0.1 mm² to about 20 mm², for example. The remaining composite section 306 can be used as an interconnecting member 310.

In various embodiments, the integrated sensor assembly, for example, as those shown in FIGS. 2A-2C, and/or FIGS. 3A-3C, can further attach a connector member (not shown in FIGS. 2A-2C or FIGS. 3A-3C). The connector member can include any suitable termination connect as known in the related art and can be configured at the other end of the interconnected element 210 and/or 310. The connector member can be further connected to the desired signal processing component (see 155) including measurement instrument, display device, transmission apparatus, and/or recording apparatus. In an exemplary embodiment, the connector member can be a metal crimp type, barrel and pin connector, a friction clamp type banana pin, or any suitable or otherwise conventional connector as known to one of ordinary skill in the art.

In various embodiments, the connector member can be an integrated fiber-rich composite type connector that is similar to the sensor element 220 or 320 as described in FIGS. 2-3 and can be fabricated by the similar compositing processes used to produce the fiber-rich composite sensor members on the other end of the interconnecting member 210 and/or 310. In various embodiments, the connector member can have a tapered pin-like projection configured on its end and/or hollow "shaped" center with a fiber rich composite forming the walls. In one embodiment, the terminal end of the connector member can be solder-attached to suitable signal processing devices. In other embodiments, the hollow connector ends can be joined to vacuum and/or pressure source or to a fluid system with its alternate probe ends exposed, sealed or gated.

In various embodiments, the disclosed integrated sensor assembly, including the interconnecting member, the sensor member, and/or the connector member, can provide high performance and can be in macroscopic size, microscopic or nanoscopic size.

For example, miniature sensors and or actuators or stimulators and/or their large arrays can be formed with each sensor having high performance and readily manufactured in microscopic-sizes, wherein the contact areas can be in the range of less than about 500 $\mu m^2$, for example, in order to enable signal probing, manipulation, stimulation at/within the cell level. In an additional embodiment, the contact area for miniature sensors and/or their arrays can be less than about 1 $\mu m^2$.

In various embodiments, nanoscale fibers or filaments including, for example, nanotubes or nanowires, nanoshafts, nanopillars, nanorods, or nanoneedles can be used for the assemblies shown in FIGS. 2A-2C and FIGS. 3A-3C to form miniature sensor members and their arrays.

Figure 4A:
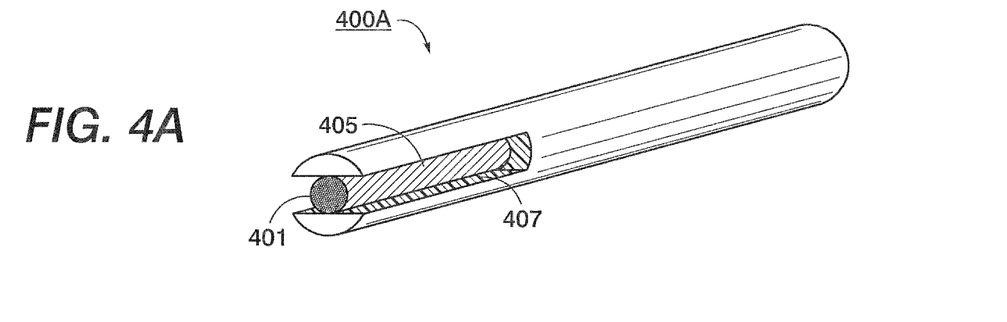
FIGS. 4A-4C depict a third exemplary integrated sensor assembly at various stages of formation in accordance with the present teachings.
Figure 4B:
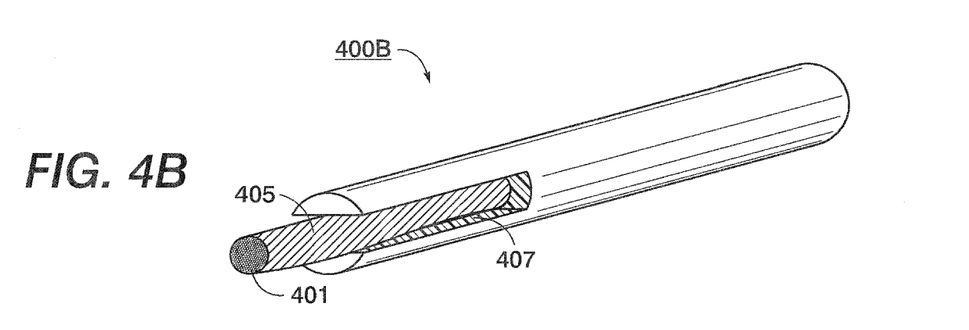
Figure 4C:
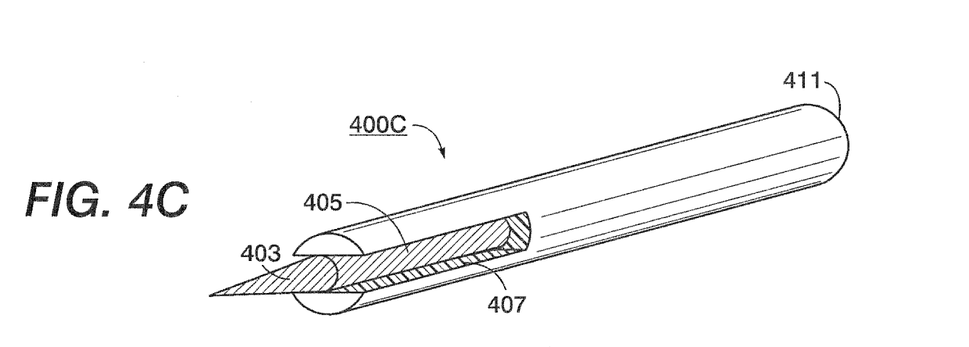

FIGS. 4A-4C depict an additional exemplary integrated sensor assembly and its arrays at various stages of formation in accordance with the present teachings.

As shown in FIG. 4A, a polymer encased member 400A can be formed including a core element 405 in nano-scale. In one embodiment, the nanoscale core element 405 can include continuous carbon nanotube (CNT) filament(s) or other filaments made from nanostructures, including compacted nanosize particulate powder. In various embodiments, the exemplary CNT filaments can provide sufficient strength, chemical inertness, x-ray and magnetic transparency, and electrical conductivity and can be commercially available. For example, CNT continuous filament(s) can be supplied from NanoComp, Concord, N.H. Any suitable insulating polymeric overcoat layer 407 or jacket layer as disclosed herein can be fabricated to encase the exemplary CNT core element.

In FIG. 4B, a portion of the polymeric overcoat layer 407 can be removed from at least a portion of one end (e.g., 401) of the polymer encased member 400A, whereby exposing a portion of the nanoscale core element 405. Various known processes, for example, laser wire-stripping methods, can be used to remove the portion of the polymeric overcoat layer and to expose, e.g., monofilament CNT core(s). In an exemplary embodiment, about 6 mm of insulating jacket can be removed from one, or both ends of the polymer encased CNT member having a length of about 2 meters, for example.

In FIG. 4C, the exposed monofilament CNT core can be processed to form a tip region 403 shaped to serve as the contact or probe for connecting with other devices of the sensing system, such as the test subject 105 of the system shown in FIG. 1. In an exemplary embodiment, exposed nanoscale core can be formed to have a needle-like pointed tip region by using a process including, e.g., arc ablation, laser ablation or other suitable process.

In various embodiments, the remaining polymer encased region can be used as a miniature integrated sensor member and interconnecting member with an appropriate terminated end. For example, the remaining polymer encased region can form miniature integrated non-metallic non-magnetic non-interacting sensor and interconnecting wire, which can be useful for probing cell or tissue level characteristics where light, magnetic or electromagnetic energy can be simultaneously used to stimulate the test subject. In various embodiments, the other end 411 of the device 400C, where the monofilament CNT core may or may not be exposed, can be terminated by any suitable connector member as described herein.

In various embodiments, other configurations of sensors can be included. In one exemplary configuration, a relatively large number of continuous and flexible CNT fibers (rather than a fiber tow as compared with that shown in FIGS. 3A-3C) can be projected from an encased element. At least one end of the number of continuous and flexible CNT fibers can be terminated by compositing a short length of the free fibers with a suitable binder polymer and mechanically forming the tip region to make a thin cross section of a fiber rich composite. The formed thin element can be flexible and suitable for use as a self loading sensor member.

In another exemplary configuration, similar to the first configuration example above, a short length of free fibers can project from a region along the length of polymer encased member, wherein a free length of fibers can be exposed by removing al least one portion of the polymer overcoat and impregnated with a suitable binder polymer, same or different from the polymer overcoat, and shape-controlled to form a flexible sensor member. Several sensor or stimulate regions can thereby be formed along a long length of the wire.

In an additional exemplary configuration, one or more nano-sized core filament(s) with suitable polymer jacket can be used to form a composite. A short length of the filament can be exposed and optionally combined with a suitable coating and optionally shaped into a suitable shaped contact sensor or stimulation.

In various embodiments, arrays of integrated sensor assembly can be formed by further assembling multiple devices, such as the devices shown in FIGS. 2A-2C, FIGS. 3A-3C and/or FIGS. 4A-4C into arrays using similar manufacturing methods for each integrated sensor assembly of the arrays. Each integrated sensor assembly can include, for example, a sensor member, an actuator member, a stimulator member, an interconnected member and/or a connector member, wherein the connector member can be connected with a signal sensing device (e.g., 155 of FIG. 1) and the other contact end of the sensor member can be connected with a test subject (e.g., 115 of FIG. 1). In various embodiments, multi-conductor ribbon-type cables as known to one of ordinary skill in the art can be used for the arrays of the integrated sensor assembly. In this case, multiple CNT filaments, for example, can be aligned to have desired inter-filament spacing and then held in position as they are simultaneously drawn through a suitable jacket coating process to form a polymer encased member having multiple core members encased with the polymer coating.

In various embodiments, the materials, devices and their methods for the disclosed integrated sensor assemblies, arrays, and related sensing systems can provide, for example, feasibility of manufacturing, desired size spectrum, and efficient and low cost mass manufacture of the eventual commercial devices, which can be useful for, for example, cell or tissue level measurements and can also be used in combination with suitable tip overcoatings to render them responsive to pH or to the presence of certain inorganic or organic chemicals. Thus, the integrated sensors can be useful in homeland security applications where simultaneous x-ray, magnet or electromagnetic energy is used within the test environment.

EXAMPLES

Example 1

Preparation of an Integrated Sensor Assembly

A length of about 1 meter of resistive carbon fiber tow (supplied by MTLS/Hexel, identified as 3K, tow lot #043) was used to form a prototype of the subject integrated sensor assembly wherein about 98% of the tow's length was left in its original state. The original shape of the carbon fiber tow appeared from oval to nearly round along its length having a diameter of approximately 0.5 mm to about 0.6 mm.

A short section of the carbon fiber tow of about 6 mm in length, containing about 3,000 individual continuous about 6-8 micron carbon fibers was left attached to the long fiber tow and used to make the sensor member.

A mixture of about 90 weight percentage catalyzed EPON epoxy 862 and about 10 weight percentage toluene was impregnated into the long section of the fibers with no resin-solvent solution wicking or flowing along the length of the tow into the remaining short section. The sample was allowed sufficient time to evaporate most of the toluene, i.e., about 15 minutes under lab ambient conditions and then was clamped between two 1 mm thick Teflon sheets (about 1 inch wide and 2 inch long) and placed in a circulating air oven and cured for 1 hour at 60° C. and then post cured for 1 hour at 130° C. The resulting fiber rich thin composite end section was solid, very strong, and exhibited a spring-like flexible response when compressed along its length-wise axis. Its thickness was approximately 0.05 mm thick and width was approximately 4 mm. The remaining short length of the original fiber tow remained essentially unchanged during this process.

Mechanical compression of the dry fiber mass was used to configure the fibers in the short region into a relatively wide and thin layer, where the objective was to dramatically change the shape within this region from near-oval to a thin, flat and ribbon-like structure. An electrical continuity test using a conventional laboratory volt-ohm meter (VOM) meter was performed to confirm that the composite end and the fiber tow region were interconnected electrically, and that little, if no, resistance change can be detected between the regions when normalized for length.

Example 2

Preparation of an Integrated Sensor Assembly

A sample length of about 500 foot long of the resistive carbon fiber tow as in the Example 1 was formed into a long solid rod having a round shape and a diameter of about 0.022 inches to about 0.023 inches (about 0.5 mm to about 0.6 mm) by use of a commercial pultrusion process (DFI, Hickory N.C.). The same thermosetting epoxy (EPON 862) as in Example 1 was used as the binder resin to secure the fibers into the round-shaped rod, but in this case there was no toluene used as a solvent. The formed composite rod sample was estimated to contain carbon fiber of about 95% to about 98% by weight and contain epoxy resin of about 2-5% by weight of the composite rod. The rod was strong and flexible, although not as flexible as the free fiber tow.

A short length of rod was laser milled (Resonetics, Nashua, N.H.) down to a diameter of about 0.012 inches and a polymeric overcoat (viz. Endstop photomask) was applied in liquid form to and dried upon the selected regions near the tip-most end and UV light cured to fully solidify the polymer onto the rod's circumference.

Example 3

Preparation of Nano-Scaled Integrated Sensor Assembly

A length of 50 μm carbon nanotube (CNT) continuous filament of approximately 20 meters in length was obtained from NanoComp (Concord, N.H.), providing sufficient strength, chemical inertness, x-ray and magnetic transparency, and electrical conductivity to serve as a suitable wire core member for the assembly described herein. A suitable insulating polymeric overcoat layer can be fabricated by solution dip coating in a thin layer to encase the CNT core-wire member A length of about 2 meters of this wire can be prepared for use, where about 6 mm of insulating jacket may be removed from one or both ends by conventional laser wire-stripping methods. The exposed monofilament CNT core at one end can be arc or laser ablated to form a needle-like pointed tip region which may serve as the contact to the test subject. The other end of the wire can be terminated by a PWB header to connect to signal sensing component.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An integrated sensor assembly comprising:
   an interconnecting member;
   at least one sensor member comprising a sensor that is extended from and electrically interconnected with the interconnecting member at any location along the interconnecting member; and
   a polymer and a core element that is substantially non-metallic, wherein the core element has a continuous length which forms a part of the at least one sensor member and the interconnecting member, and extends continuously from the at least one sensor member through the interconnecting member, and the interconnecting member is configured to transmit a signal from the sensor of the at least one sensor member along the continuous length of the core to a signal processing device,
   wherein each of the at least one sensor member and the interconnecting member comprises a structure comprising a jacket layer made of the polymer and surrounding the core element, wherein the jacket layer of the sensor is discontinuous with the jacket layer of the interconnecting member
   wherein the core element comprises a single strand filament or a multi-stranded filament, wherein each strand comprises one of a fiber, a wire, a needle, a thread, a yarn, and a fabric; and wherein said filament further comprises one or more of a nanotube, nanowire, nanoscale plate, nanorod, nanofiber, or other nanostruture that has at least one dimension of about 100 nm or less.

2. The assembly of claim 1, further comprising a connector member connected to the interconnecting member for transmitting signals to a signal processing device.

3. The assembly of claim 2, wherein the connector member comprises an integrated fiber-rich composite connector.

4. The assembly of claim 1, wherein each of the at least one sensor member and the interconnecting member comprises a composite formed by compositing the core element with the polymer.

5. The assembly of claim 1, wherein the core element comprises one or more materials comprising carbon, silicon, boron, doped silicon, boron-carbon, boron-nitride, carbonized synthetic fibers, pitch carbon fibers, polyacrylonitrile carbon fibers, or graphite.

6. The assembly of claim 1, wherein the core element has a dimension of about 500 microns or less.

7. The assembly of claim 1, wherein the polymer comprises one or more of an epoxy, acetal, polyester, ionic rubber, non-ionic rubber, ionic polyurethane, non-ionic polyurethane, polyether sulfone, polyether ether ketone, polyether imide, polystyrene, polyethylene terephthalate, polyamide, polyimide, polyvinylchloride, polyphenylene oxide, polycarbonate, acrylonitrile-butadiene-styrene terpolymer, silicone, fluropolymer, polyolefin, or combinations thereof.

8. A sensing system comprising the assembly of claim 1, wherein the sensing system further comprises the signal processing device, the signal processing device being connected to the interconnecting member to process a sensing signal detected by the sensor member of the integrated sensor assembly.

9. The sensing system of claim 8, wherein the signal processing device comprises a resistor, a liquid crystal display (LCD), a multi-chip module, a printed circuit board (PCB) and/or a printed wiring board (PWB).

10. The assembly of claim 1, further comprising an array of the integrated sensor assemblies, wherein the array comprises about 2 to about 3000 integrated sensor assemblies.

\* \* \* \* \*